United States Patent [19]

Pitt

[11] 4,265,535

[45] May 5, 1981

[54] OIL-IN-WATER METHOD AND DETECTOR

[75] Inventor: Gillies D. Pitt, Saffron Walden, England

[73] Assignee: ITT Industries, Inc., New York, N.Y.

[21] Appl. No.: 33,159

[22] Filed: Apr. 25, 1979

[30] Foreign Application Priority Data

Sep. 11, 1978 [GB] United Kingdom ............... 19046/78

[51] Int. Cl.³ ...................... G01N 33/28; G01N 21/00
[52] U.S. Cl. ..................................... 356/70; 250/574;
250/575; 356/343
[58] Field of Search ................. 356/70, 343, 336, 340;
250/574, 575; 73/61 R, 61.1 R

[56] References Cited

U.S. PATENT DOCUMENTS

| 3,758,787 | 9/1973 | Sigrist | 356/340 |
| 4,078,863 | 3/1978 | Eriksson et al. | 356/336 |
| 4,146,799 | 3/1979 | Pitt et al. | 356/70 |

FOREIGN PATENT DOCUMENTS 2528912  1/1977  Fed. Rep. of Germany ........... 356/343

Primary Examiner—Alfred E. Smith
Assistant Examiner—Carolyn E. Fields
Attorney, Agent, or Firm—A. Donald Stolzy

[57] ABSTRACT

A light scattering oil-in-water detector and method. Scattered light is measured at a plurality of scattering angles, one angle being chosen such that the light scattered by the oil is substantially zero. This overcomes interference arising from suspended solids, e.g., rust.

10 Claims, 5 Drawing Figures

# OIL-IN-WATER METHOD AND DETECTOR

BACKGROUND OF THE INVENTION

This invention relates to arrangements for detecting and measuring oil in water, and more particularly to oil-in-water meters of the light scattering type and detection methods.

PRIOR ART STATEMENT

U.S. Pat. No. 4,201,471 discloses a method and apparatus including a scatter cell having means for receiving direct and scattered light transmitted therethrough, a first amplifier for receiving the scattered light output of the cell, a second logarithmic amplifier for receiving the direct light output of the cell, automatic gain control means for calibrating the amplifiers so as to match the transmission loss of the cell, means for flushing out the cell with clean water when calibration is effected, and threshold suited means for selectively enabling one of said amplifiers, and in which the switch means is so arranged that the first amplifier is enabled only below an oil concentration for which the scattered light output characteristic of the cell is substantially linear, the second amplifier being enabled above that oil concentration.

While such an arrangement has proved successful, there are some applications in which it is necessary to measure oil levels in water containing a proportion of suspended solid material, e.g., rust particles. The solid particles can in certain circumstances contribute substantially to the total intensity of scattered light from the oil-in-water mixture and thus cause false output measurements.

SUMMARY OF THE INVENTION

According to the present invention, a light beam is directed into water having oil dispersed therein, and scattered light is measured at a plurality of angles with respect to the incident light beam, one of the measurements being made at an angle at which substantially no light is scattered by the oil.

BRIEF DESCRIPTION OF THE DRAWINGS

In the accompanying drawings which illustrate exemplary embodiments of the present invention.

DESCRIPTION OF THE PREFERRED EMBODIMENTS

According to an aspect of the invention there is provided a method of measuring oil dispersed in water, including directing a light beam into the water, and measuring the light scattered at a plurality of angles with respect to the incident light beam, and in which one said measurement is made at an angle at which substantially no light is scattered by the oil.

It has been discovered in accordance with the present invention, that the intensity of light scattered both by oil droplets and solid particles varies with the scattering angle. It has also been so discovered that it is possible to determine a scattering angle at which the scattered light component corresponding to the oil droplets is substantially zero.

Further, it has been found that the oil droplet particle size distribution can be characterized sufficiently well by a selected pump and other homogenizing techniques. Such a size distribution will produce a scatter of incident light which is a nonlinear function of scattering angle. It has also been found that the oil has a relatively high scattering effect at small angles to the incident beam. This response falls substantially to zero at an angle in the range of 40 to 60 degrees with a cell of typical geometry. The oil droplet size is typically in the range of about 30 microns in diameter.

The solid particles which are normally kept in suspension (e.g., rust, dust, etc.) also give a high output at low angles, but they also provide a high output at larger angles. Thus an angle can be selected higher than 30° where only the particulates are measured (ignoring the minimal response due to the oil.) The independent measurement of the particulate concentration can be used together with the lower angle detection intensity containing components due to oil and particulates to eventually compute the oil concentration only, or to minimize the perturbing result due to other particulates.

The accuracy of this technique using a plurality not necessarily equal to, more than or less than three detectors at various angles between zero and 180 degrees can be improved, using weighting to compensate for the change of oil and solid response with angle. Microprocessor techniques may be employed to carry out the weighting, dividing and subtracting steps. The microprocessor can be programmed to respond to different particle size distributions which occur in different operating situations.

Figure 1:
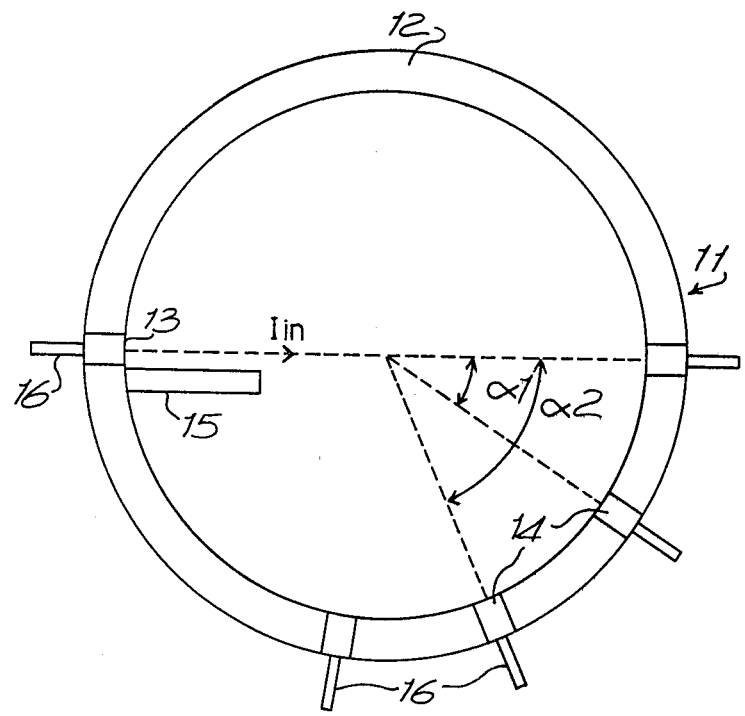
FIG. 1 is a schematic diagram of a scatter cell constructed in accordance with the present invention.

Referring to FIG. 1, a light scatter cell 11 is shown including an annular housing 12 provided with an input window 13 whereby light, e.g., from a solid state laser, can be introduced to the cell 11, and a plurality of output windows 14. A baffle 15 collimates the light beam inserted into the cell 11 thus preventing spurious reflections. The precise position of the baffle 15 is not critical provided it prevents direct light reaching the windows 14 from the input. The outlet windows 14 are arranged at various angles, $\alpha 1$, $\alpha 2$ to a light beam $I_{in}$ directed into the cell via window 13. The light outputs from the output windows 14 are coupled to respective detector and measurement circuits (not shown). Advantageously the windows 13 and 14 may be provided with fiber optic couplers 16 whereby light is led to or from the windows.

Figure 2:
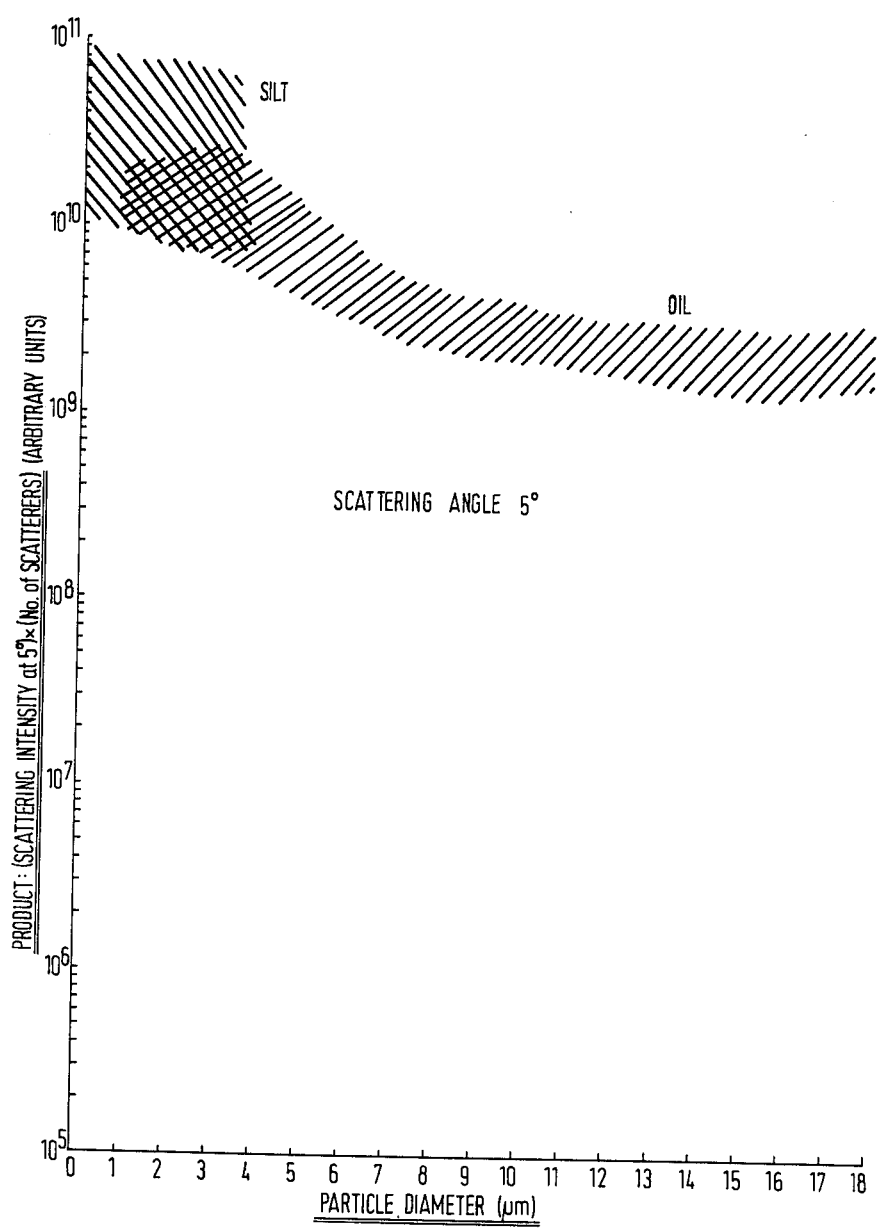
FIG. 2 is a graph showing the relationship between scattered light intensity for oil and solids at a scattering angle of 5 degrees.
Figure 3:
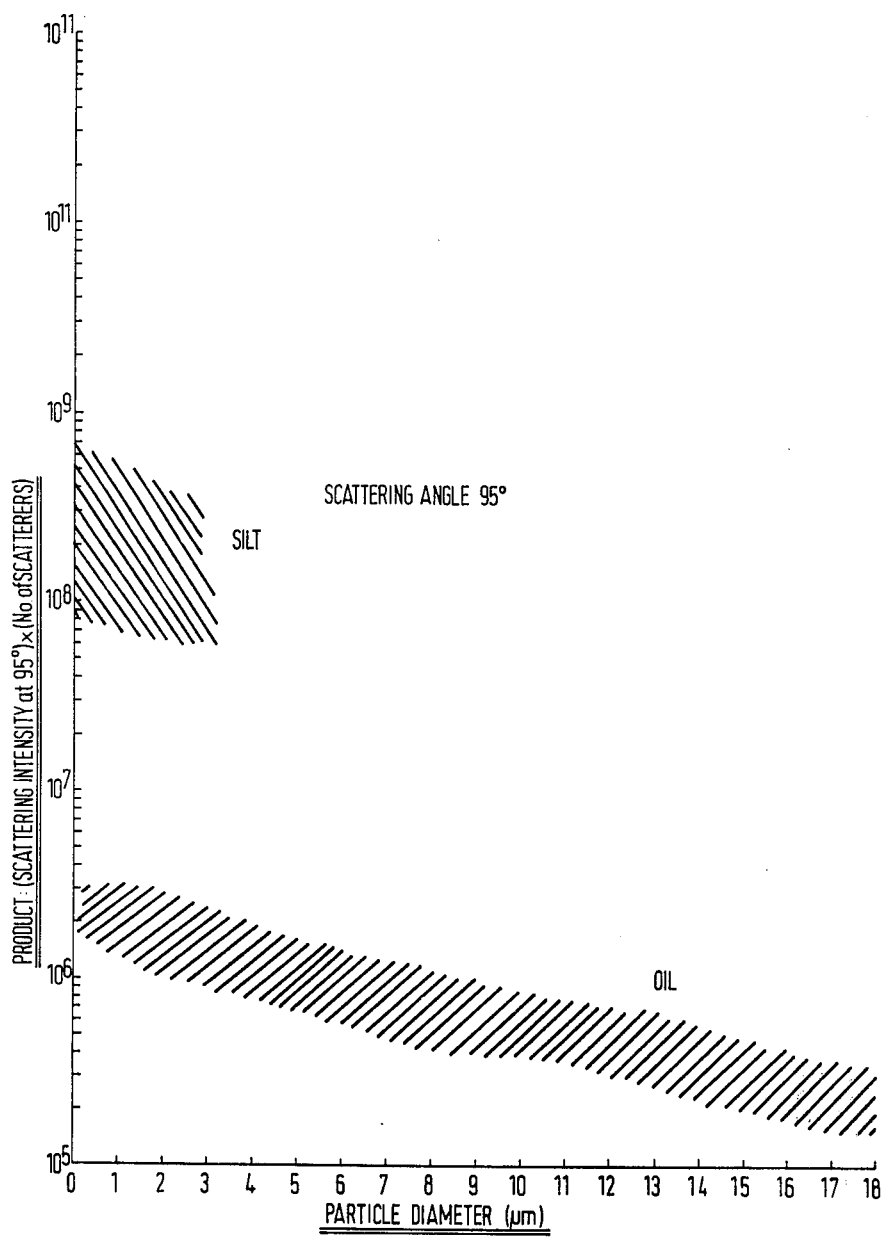
FIG. 3 is a graph showing the corresponding relationship at a scattering angle of 95 degrees.

As shown in FIGS. 2 and 3 the capacity of oil droplets or of solid particles to scatter incident light is a function of scattering angle. Thus oil (FIG. 2) has a relatively high scattering effect at small angles to an incident beam, but this response falls substantially to zero at an angle found to be in the range 40° to 180° for oil droplets having diameters up to and including 30 microns. Solid particles on the other hand show a slow reduction of scattering intensity with angle (FIG. 2). Thus by taking light intensity measurements at these two angles the interfering effect of the solid particles may be compensated for and the oil concentration determined. The necessary calculation may be performed by an electronic device, e.g., a microprocessor.

In FIGS. 2 and 3 the solid particles have diameters in the range 0-3 microns and, typically, are present at a level 30-70 ppm. The oil droplets are typically up to 18 microns diameter and are present at a level of 15 ppm. FIG. 2 shows that, at small scattering angles the responses of the solid and oil are comparable, whereas at a large scattering angle (FIG. 3) the response from the oil is insignificant compared to that of the solid. These results are given by way of example only, as different oils and different solids will of course provide different results. However, in each case there is a broadly similar relationship between the light scattering of the solid and oil.

There are at least two application areas relative to particulate and/or oil detection. That is, there are at least two areas corresponding to the different concentration ranges likely to be measured in practice.

(1) Crude oil washing or clean ballast monitoring (FIG. 4) is one. Oil concentration to alarm at 15 ±5 ppm, but with a possible background concentration of solids up to 100 ppm (usually considerably less). Oil rigs and refinery effluent applications have similar concentrations.

(2) Dirty ballast monitoring (FIG. 5) is another, i.e., where concentrations up to 1000 ppm of oil must be measured, with background solid concentrations of 100 ppm say (usually considerably less).

Figure 4:
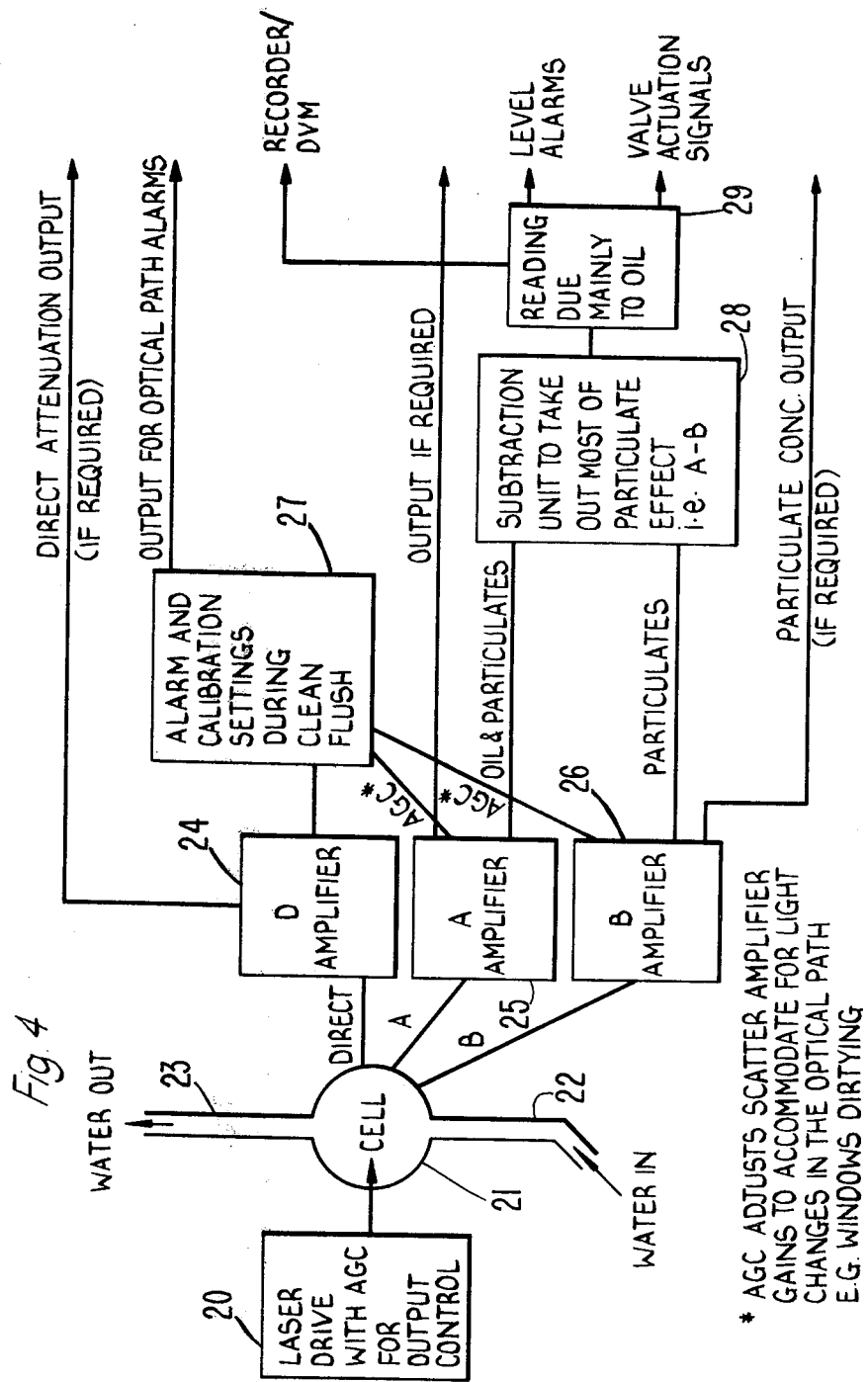
FIG. 4 is a diagrammatic view of a clean ballast monitoring system constructed in accordance with the present invention.

Relative to (1), it is expected that the major application areas will be involved. FIG. 4 is a block diagram showing the subtraction effect involving scatter detectors. It should be noted that the signals obtained at the detectors are suitably processed and amplified before the subtraction process. Outputs may be available for displays from each detector should, for example, the user wish to have a reading of the solid content only. Amplifiers 25 and 26 produce output signals directly proportional to signals A and B, respectively, in the output (A−B) of circuit 29.

Relative to (2), dirty ballast monitoring application involving a subtraction of the particulates can be quite complex. At present, with no subtraction involved, there is a switch-over when the direct attenuated voltage falls below a certain set valve (typically at a concentration of 200 ppm). At high concentrations there is simple measurement on the direct beam (i.e., a changeover from scatter to direct). The incorporation of subtraction techniques with this system at high concentrations will therefore involve extra switching circuitry.

Figure 5:
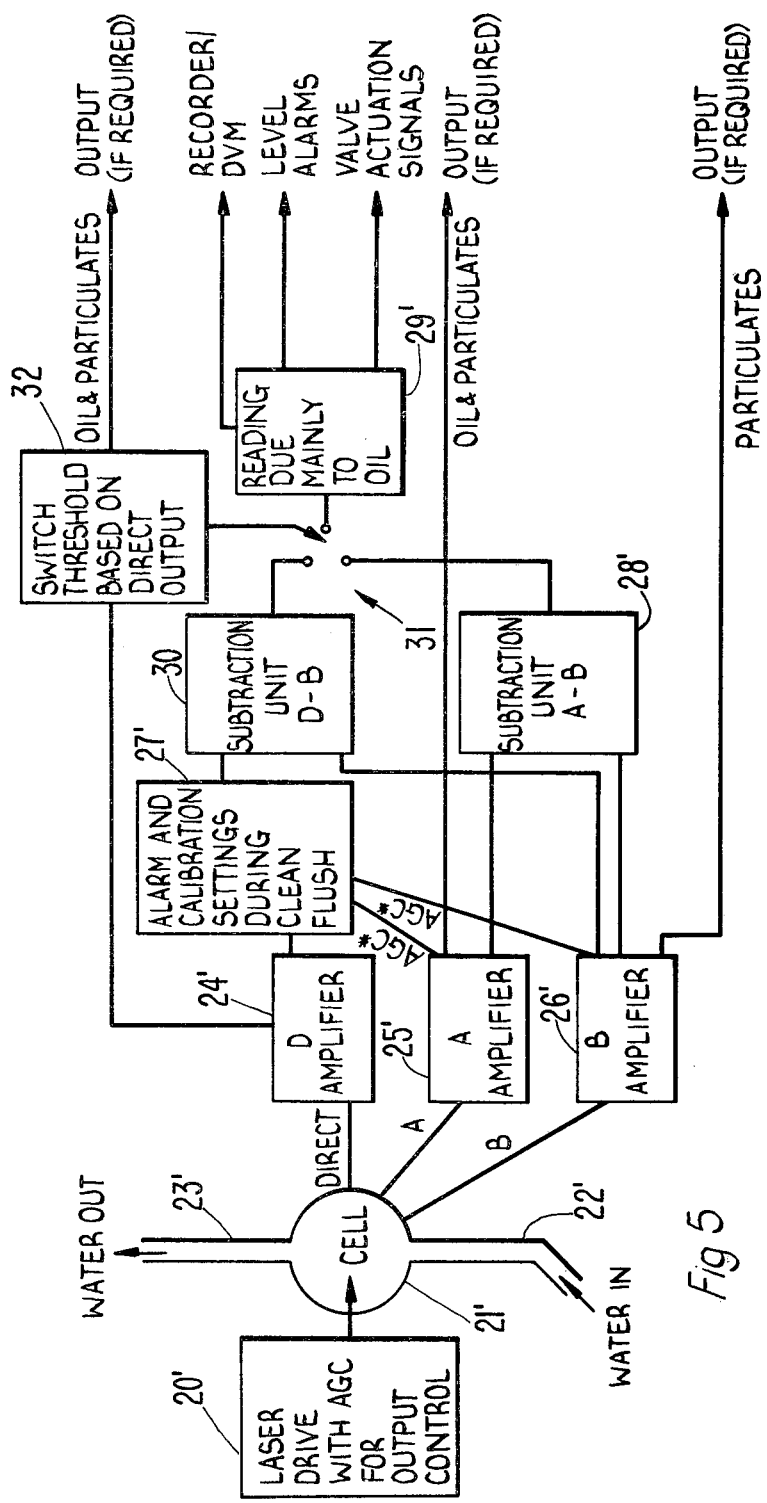
FIG. 5 is a diagrammatic view of a dirty ballast monitoring system constructed in accordance with the present invention.

When the total concentration of oil plus solids, as measured on the direct detector, is less than the switch-over point, the subtraction will involve the scatter detectors as for case (1). However, above the critical switch-over point the subtraction will involve D−B, where D is directly proportional to the output of amplifier 24 or the output of amplifier 24'. The switching for this maneuver could occur with the signals at different stages of processing. FIG. 5 shows one possible solution which might be used, where the switching is governed by the direct signal in order to pass on the relevant subtracted signal. In FIG. 5 it is proposed that both subtractions are carried out, i.e., A−B and D−B, but at total direct concentrations above 200 ppm the output from D−B is used for display.

The relative gains of amplifiers 25 and 26 must be set such that the gain of amplifier 25 is larger than that of amplifier 26, i.e., so that the reading stays positive. Emphasis may be placed on case (1), since in (2) the relative importance of extraneous particulates is smaller. Hence FIG. 5 could be simplified if it is found in practice that at high concentrations a subtraction effect involving the direct beam may not be necessary.

In FIG. 4, a laser drive 20 is provided with an automatic gain control (AGC) for output control.

Laser drive 20 supplies coherent light to a cell 21 in a direction the same as or similar to the horizontal dotted line in FIG. 1. Water is supplied to cell 21 via a conduit 22 and exits via a conduit 23.

Amplifiers 24, 25 and 26 are connected from cell 21 to receive direct light and light at angles of, for example, $\alpha_1$ and $\alpha_2$ (see FIG. 1). The outputs of amplifiers 24, 25 and 26 are connected to an alarm 27. Amplifiers 25 and 26 have outputs with signals of amplitudes A and B, respectively, connected to a subtraction unit 28. The output of unit 28 is A−B or the difference between the output signals of amplifiers 25 and 26. A−B is then impressed upon an output circuit 29.

In FIG. 5 a laser drive 20', a cell 21', a conduit 22', a conduit 23', and amplifiers 24', 25' and 26' may be the same and connected in the same ways as structures 20, 21, 22, 23, 24, 25 and 26, respectively, shown in FIG. 4. The same is true of alarm 27', unit 28', and circuit 29' relative to 27, 28 and 29.

A subtraction unit 30 produces an output D−B to a switch 31. D−B is proportional to the difference between the respective outputs of amplifiers 24' and 26'. Switch 31 is operated by a threshold detector 32.

What is claimed is:

1. In the scatter cell apparatus for an oil-in-water meter of the type in which oil concentration is determined by the scattering effect of the oil on an incident light beam, a scatter cell comprising: a housing having an input window for said light beam and a plurality of output windows arranged each at a different angle to said light beam at least one of, said output windows being disposed with respect to the incident beam at an angle at which the intensity of light scattered from the oil has a minimum value.

2. A cell as claimed in claim 1, and in which one of said output windows is disposed in line with the incident beam.

3. A cell as claimed in claim 1 or 2, and in which one of said windows is disposed at an angle which is less than 40 degrees to the incident beam, and another of said windows is disposed at an angle which is greater than 40 degrees to the incident beam.

4. A scatter cell as claimed in claim 1 or 2 and in which said windows are provided each with a fiber optic coupling whereby light is led to or from the window.

5. Apparatus for detecting the concentration of oil in water, said apparatus comprising: a light beam source; a scatter cell having an annular periphery with a first window to admit light from said source to the interior of said scatter cell, light passing through said first window also passing through the fluid inside said scatter cell in a predetermined direction across the interior thereof, said scatter cell containing oil droplets and particulates in a water suspension, said scatter cell having at least second and third windows to receive light which has passed through said fluid, said second and third windows being disposed at first and second different respective angles relative to said predetermined direction from the center of said scatter cell, said first angle being larger than said second angle; first amplifier means and second amplifier means connected from said second and third windows, respectively, for producing first and second output signals, respectively, proportional to the light outputs of said second and third windows, respectively; and subtraction means connected from said first and second amplifier means for producing a third output signal proportional to the difference between the amplitudes of said first and second output signals; said second angle being small enough to cause said second amplifier means to produce said second output signal at a magnitude proportional to the sum of the concentration of said oil droplets in said water and the concentration of said particulates in said water; said first angle being large enough to cause said first amplifier means to produce said first output signal at a magnitude proportional to the concentration of said particulates in said water, but effectively independent of the concentration of said oil droplets in said water.

6. The invention as defined in claim 5, wherein an indicator calibrated in oil concentration is connected from said subtraction means.

7. The invention as defined in claim 6, wherein said second angle is smaller than 40 degrees, and said first angle is greater than 40 degrees.

8. The invention as defined in claim 5, wherein said second angle is smaller than 40 degrees, and said first angle is greater than 40 degrees.

9. The apparatus as defined in claim 8, wherein said second angle is about 5 degrees, and said first angle is about 95 degrees.

10. The apparatus as defined in claim 9, wherein an indicator calibrated in oil concentration is connected from said subtraction means.

* * * * *